(12) United States Patent
Nishikori et al.

(10) Patent No.: US 12,288,622 B2
(45) Date of Patent: Apr. 29, 2025

(54) MEDICAL IMAGE DIAGNOSTIC APPARATUS, MEDICAL IMAGE PROCESSING APPARATUS, AND MEDICAL IMAGE PROCESSING SYSTEM

(71) Applicant: CANON MEDICAL SYSTEMS CORPORATION, Tochigi (JP)

(72) Inventors: Akira Nishikori, Utsunomiya (JP); Tatsuya Watanabe, Nasushiobara (JP); Jun Ooshima, Nasushiobara (JP); Yohei Minatoya, Nasushiobara (JP); Ryo Okuda, Utsunomiya (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 491 days.

(21) Appl. No.: 17/658,357

(22) Filed: Apr. 7, 2022

(65) Prior Publication Data
US 2022/0328196 A1 Oct. 13, 2022

(30) Foreign Application Priority Data
Apr. 8, 2021 (JP) ................................. 2021-065734

(51) Int. Cl.
*G16H 50/30* (2018.01)
*G06T 7/00* (2017.01)
*G16H 30/40* (2018.01)
*G16H 40/20* (2018.01)

(52) U.S. Cl.
CPC .......... *G16H 50/30* (2018.01); *G06T 7/0012* (2013.01); *G16H 30/40* (2018.01); *G16H 40/20* (2018.01); *G06T 2207/10081* (2013.01)

(58) Field of Classification Search
CPC ........ G16H 50/30; G16H 30/40; G16H 40/20; G16H 30/20; G16H 50/20; G06T 7/0012; G06T 2207/10081; A61B 6/032
See application file for complete search history.

(56) References Cited

U.S. PATENT DOCUMENTS 9,924,867 B2 * 3/2018 Abramoff ................ A61B 3/12
2002/0094119 A1 * 7/2002 Sahadevan ............ G16H 30/40
382/132

(Continued)

FOREIGN PATENT DOCUMENTS

JP 2002-132962 A 5/2002
JP 2003-290191 A 10/2003

(Continued)

OTHER PUBLICATIONS

Japanese Office Action issued Nov. 27, 2024 in Japanese Patent Application No. 2021-065734, 3 pages.

*Primary Examiner* — Roy M Punnoose
(74) *Attorney, Agent, or Firm* — Oblon, McClelland, Maier & Neustadt, L.L.P.

(57) ABSTRACT

A medical image diagnostic apparatus according to an embodiment includes processing circuitry and a display. The processing circuitry acquires medical images. The processing circuitry sends the medical images to a medical image processing apparatus that performs disease analysis based on the medical images. The processing circuitry receives the analysis result from the medical image processing apparatus. The display displays warning information based on the analysis result.

9 Claims, 12 Drawing Sheets

(56) References Cited

U.S. PATENT DOCUMENTS

| | | | |
|---|---|---|---|
| 2004/0186357 A1* | 9/2004 | Soderberg | A61B 5/681 |
| | | | 600/300 |
| 2008/0292169 A1* | 11/2008 | Wang | G06T 7/174 |
| | | | 382/131 |
| 2012/0263368 A1* | 10/2012 | Nakano | G16H 50/30 |
| | | | 382/133 |
| 2014/0378810 A1* | 12/2014 | Davis | G06F 16/248 |
| | | | 600/407 |
| 2015/0199121 A1* | 7/2015 | Gulaka | G06F 3/0482 |
| | | | 715/771 |
| 2016/0148375 A1* | 5/2016 | Oh | A61B 6/505 |
| | | | 382/131 |
| 2016/0224229 A1* | 8/2016 | Jo | G06T 7/0012 |
| 2019/0117812 A1 | 4/2019 | Olsen et al. | |
| 2020/0327979 A1* | 10/2020 | Ishii | G06T 7/0014 |
| 2021/0259664 A1* | 8/2021 | Hare | G06N 3/047 |
| 2021/0272277 A1* | 9/2021 | Ogino | G06N 20/00 |
| 2022/0012878 A1* | 1/2022 | Aoyama | G06T 11/00 |

FOREIGN PATENT DOCUMENTS

| | | |
|---|---|---|
| JP | 2017-202310 A | 11/2017 |
| JP | 2019-139602 A | 8/2019 |
| JP | 2020-173614 A | 10/2020 |
| WO | WO 2020/260540 A1 | 12/2020 |

* cited by examiner

FIG.5

| MESSAGE ID | DATA FORMAT |
|---|---|
| SOURCE IP | IPv4 / IPv6 |
| SOURCE APPARATUS ID/ NAME | NUMERICAL VALUE # SIZE/ STRING |
| DESTINATION IP | IPv4 / IPv6 |
| DESTINATION APPARATUS ID/NAME | NUMERICAL VALUE # SIZE/ STRING |
| Flag_urgency | EITHER ONE OF URGENT, WARNING, AND INFO |
| MESSAGE CONTENT | STRING |
| CONCERNED EXAMINATION ID | STRING |
| CONCERNED SUBJECT ID | STRING |

MEDICAL IMAGE DIAGNOSTIC APPARATUS, MEDICAL IMAGE PROCESSING APPARATUS, AND MEDICAL IMAGE PROCESSING SYSTEM

CROSS-REFERENCE TO RELATED APPLICATIONS

This application is based upon and claims the benefit of priority from Japanese Patent Application No. 2021-065734, filed on Apr. 8, 2021; the entire contents of which are incorporated herein by reference.

FIELD

Embodiments described herein relate generally to a medical image diagnostic apparatus, a medical image processing apparatus, and a medical image processing system.

BACKGROUND

Typically, a medical image diagnostic apparatus is not equipped with the function of determining whether or not the subject for whom the imaging has been performed is suffering from an infectious disease or an acute disease leading to death if its findings are missed (hereinafter, this is called "killer disease"). On the other hand, as a technology for supporting differential diagnosis, an analysis application such as the computer-aided diagnosis (CADx) is known and is used with the aim of supporting the diagnosis made by the doctor.

BRIEF DESCRIPTION OF THE DRAWINGS

FIG. 5 is a diagram for explaining an example of the data sent and received by the medical image processing system according to the first embodiment;

DETAILED DESCRIPTION

Figure 1:
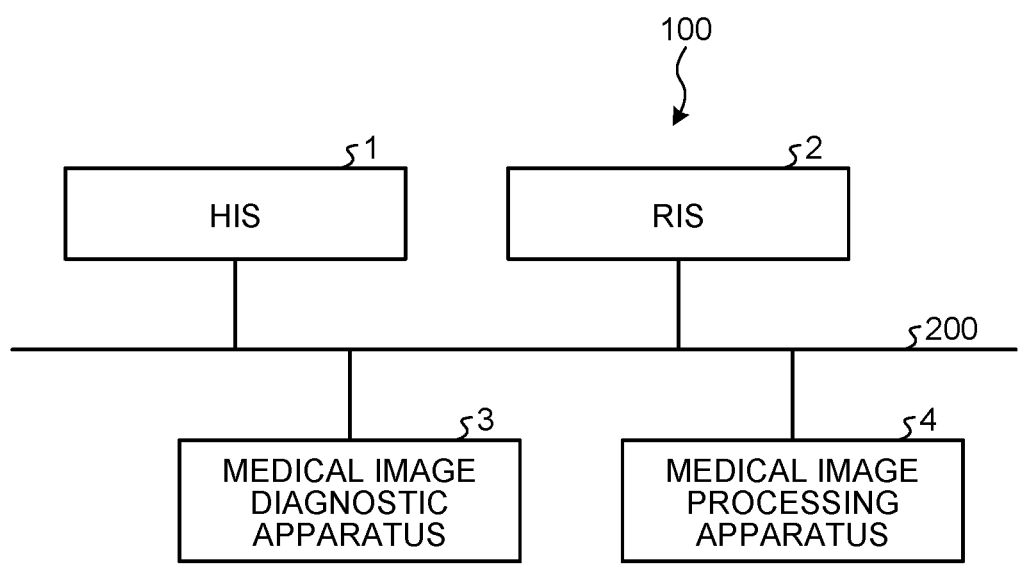
FIG. 1 is a diagram illustrating an exemplary configuration of a medical image processing system according to a first embodiment.

According to an embodiment, a medical image diagnostic apparatus includes processing circuitry and a display. The processing circuitry is configured to acquire a medical image. The processing circuitry is configured to send the medical image to a medical image processing apparatus which performs disease analysis based on the medical image. The processing circuitry is configured to receive analysis result from the medical image processing apparatus. The display is configured to display warning information based on the analysis result.

Exemplary embodiments of a medical image diagnostic apparatus, a medical image processing apparatus, and a medical image processing system are described below in detail with reference to the accompany drawings. However, the medical image diagnostic apparatus, the medical image processing apparatus, and the medical image processing system according to the application concerned are not limited by the embodiments described below. Moreover, in the following explanation, identical constituent elements are referred to by the same reference numerals, and their explanation is not given repeatedly.

First Embodiment

FIG. 1 is a diagram illustrating an exemplary configuration of a medical image processing system 100 according to a first embodiment. As illustrated in FIG. 1, the medical image processing system 100 includes a hospital information system (HIS) 1, a radiology information system (RIS) 2, a medical image diagnostic apparatus 3, and a medical image processing apparatus 4 that are communicably connected to each other via a network 200. For example, the medical image processing system 100 is built using an in-hospital local area network (LAN) installed in the concerned hospital. Meanwhile, to the network 200 illustrated in FIG. 1, various other types of apparatuses and systems can also be connected.

The HIS 1 includes an HIS server and terminal devices that are connected to the other apparatuses and systems connected to the network 200, and that communicate a variety of information with the other apparatuses and systems. For example, the HIS 1 sends subject information and order information to the other apparatuses and systems, and receives reports of the operation results from the other apparatuses and systems. Moreover, in response to the requests received from the other apparatuses and systems, the HIS 1 sends operation results and reference information.

The RIS 2 includes an RIS server and a terminal device that are connected to the other apparatuses and systems connected to the network 200, and that communicate a variety of information with the other apparatuses and systems. For example, the RIS 2 communicates a variety of information related to the examination task with the other apparatuses and systems. Moreover, in response to the requests received from the other apparatuses and systems, the RIS 2 sends the examination results.

The medical image diagnostic apparatus 3 is an apparatus of one of various types meant for examining a subject. Examples of the medical image diagnostic apparatus 3 include an X-ray diagnostic apparatus, an X-ray CT apparatus (CT stands for Computed Tomography), an MRI apparatus (MRI stands for Magnetic Resonance Imaging), an ultrasonography apparatus, an endoscopy apparatus, a SPECT apparatus (SPECT stands for Single Photon Emission Computed Tomography), and a PET apparatus (PET stands for Positron Emission computed Tomography). The medical image diagnostic apparatus 3 acquires image data (medical images) from the subject; sends the acquired image data to the medical image processing apparatus 4; and receives the result of analysis of the image data from the medical image processing apparatus 4.

The medical image processing apparatus 4 receives image data from the medical image diagnostic apparatus 3, analyzes the image data, and sends the analysis result to the medical image diagnostic apparatus 3. For example, the medical image processing apparatus 4 is implemented using a computer device such as a server, a workstation, or a personal computer.

Given below is the explanation of a detailed configuration of the medical image diagnostic apparatus 3 and the medical image processing apparatus 4 according to the first embodiment. In the first embodiment, an X-ray CT apparatus 3a represents an example of the medical image diagnostic apparatus 3.

Figure 2:
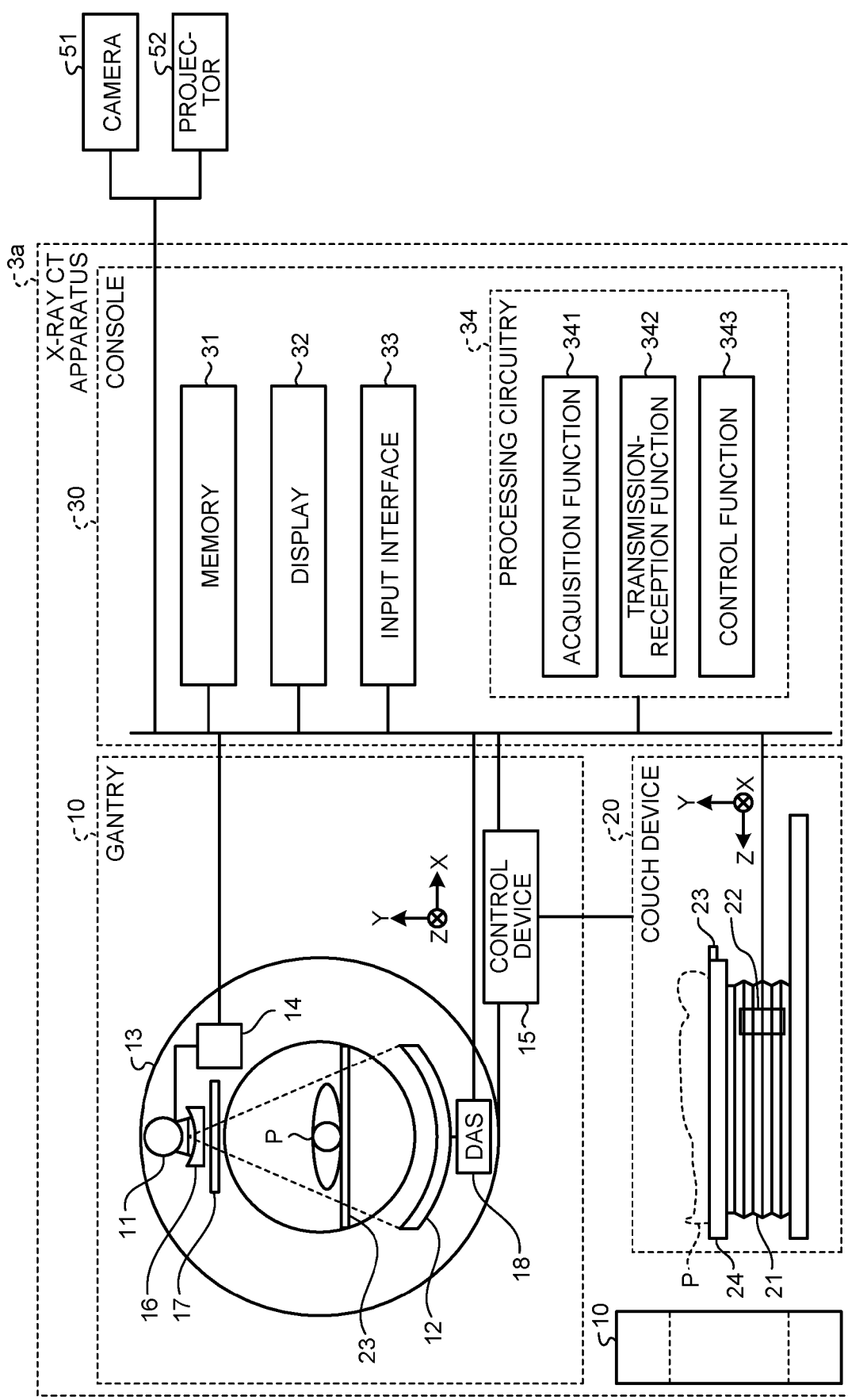
FIG. 2 is a diagram illustrating an exemplary configuration of an X-ray CT apparatus according to the first embodiment.

FIG. 2 is a diagram illustrating an exemplary configuration of the X-ray CT apparatus 3a according to the first embodiment. As illustrated in FIG. 2, the X-ray CT apparatus 3a according to the first embodiment includes a gantry 10, a couch device 20, and a console 30; and is connected to a camera 51 and a projector 52.

The camera 51 takes images of the inside of an examination room in which the X-ray CT apparatus 3a is installed. More particularly, the camera 51 acquires images of the surrounding of the X-ray CT apparatus 3a and sends the acquired images to the X-ray CT apparatus 3a. The projector 52 projects a light in the examination room under the control of the X-ray CT apparatus 3a. More particularly, the projector 52 illuminates the positions in the examination room with which the subject and the operator came in contact.

The gantry 10 includes an X-ray tube 11, an X-ray detector 12, a rotatable frame 13, an X-ray high-voltage generator 14, a control device 15, a wedge 16, a collimator 17, and a data acquisition system (DAS) 18.

The X-ray tube 11 includes a cathode (filament) for generating thermal electrons, and includes an anode (target) for generating X-rays upon being subjected to collision of thermal electrons. In the X-ray tube 11, when a high voltage is applied from the X-ray high-voltage generator 14, thermal electrons are radiated from the cathode toward the anode, thereby resulting in the generation of X-rays with which a subject P is to be irradiated.

The X-ray detector 12 includes a plurality of detection elements for detecting X-rays. Each detection element of the X-ray detector 12 detects X-rays that were radiated from the X-ray tube 11 and that passed through the subject P, and outputs signals corresponding to the detected X-ray dosage. For example, the X-ray detector 12 includes a plurality of detection element arrays in each of which a plurality of detection elements is arranged in a channel direction along a single arc centered on the focal point of the X-ray tube 11. For example, the X-ray detector 12 has a structure in which a plurality of detection element arrays, in each of which a plurality of detection arrays is arranged in a channel direction, is arranged in row directions (slice directions). Meanwhile, the X-ray detector 12 either can be of the indirect conversion type or can be of the direct conversion type.

The rotatable frame 13 is a toric frame that supports the X-ray tube 11 and the X-ray detector 12 from opposite sides, and enables rotation of the X-ray tube 11 and the X-ray detector 12 under the control of the control device 15. The X-ray high-voltage generator 14 includes electrical circuitry such as a transformer and a rectifier; includes a high-voltage generating device that generates a high voltage to be applied to the X-ray tube 11; and an X-ray control device that performs control of the output voltage according to the X-rays generated by the X-ray tube 11.

The control device 15 includes processing circuitry such as a central processing unit (CPU), and includes drive mechanisms such as a motor and an actuator. The control device 15 receives input signals from an input interface 42, and accordingly controls the operations of the gantry 10 and the couch device 20.

The wedge 16 is a filter for adjusting the X-ray dosage radiated from the X-ray tube 11. For example, the wedge 16 is a wedge filter or a bow-tie filter formed by processing aluminum to have a predetermined target angle or a predetermined thickness. The collimator 17 is a lead sheet meant for narrowing down the area being irradiated by the X-rays that have passed through the wedge 16, and a slit is formed as a result of combining a plurality of lead sheets.

The DAS 18 acquires the signals of the X-rays detected by the detection elements of the X-ray detector 12. For example, the DAS 18 includes an amplifier that amplifies the electrical signals output from each detection element and includes an A/D converter that converts the electrical signals into digital signals; and accordingly generates detection data. The DAS 18 is implemented using, for example, a processor.

The couch device 20 is a device on which the target subject P for imaging is positioned and is then moved; and includes a base 21, a couch driving device 22, a couchtop 23, and a supporting frame 24. The base 21 is a housing that supports the supporting frame 24 to be movable in the vertical direction. The couch driving device 22 is a drive mechanism for moving the couchtop 23, on which the subject P is positioned, in the long axis direction of the couchtop 23; and includes a motor and an actuator. The couchtop 23 is disposed on the top surface of the supporting frame 24, and is a bedplate on which the subject P is positioned.

The console 30 includes a memory 31, a display 32, an input interface 33, and processing circuitry 34.

The memory 31 is implemented, for example, using a semiconductor memory device such as a random access memory (RAM) or a flash memory; or using a hard disk; or using an optical disk. The memory 31 is used to store, for example, projection data and CT image data. Moreover, the memory 31 is used to store computer programs that enable the circuitry in the X-ray CT apparatus 3a to implement their functions.

The display 32 is used to display a variety of information. For example, the display 32 is used to display various images generated by the processing circuitry 34, and displays a graphical user interface (GUI) meant for receiving various operations from the operator. Moreover, the display 32 is used to display the analysis result obtained by the medical image processing apparatus 4. Regarding the analysis result obtained by the medical image processing apparatus 4, the detailed explanation is given later. The display 32 is implemented using, for example, a liquid crystal display, a cathode ray tube (CRT) display, an organic electroluminescence (EL) display, a plasma display, or a touch-sensitive panel. Herein, the display 32 either can be a display included in the console 30, or can be a display included in the gantry 10. Meanwhile, the display 32 represents an example of a display.

The input interface 33 receives various input operations from the operator, converts the received input operations into electrical signals, and outputs the electrical signals to the processing circuitry 34. For example, the input interface 33 receives, from the operator, an input operation for inputting the scanning conditions, or inputting the reconstruction conditions to be applied at the time of reconstructing the CT Image data, or inputting the image processing conditions to be applied at the time of generating postprocessing data from the CT image data.

The input interface 33 is implemented, for example, using a mouse; or using a keyboard; or using a trackball; or using switches; or using buttons; or using a joystick; or using a touchpad for performing input operations by touching an operation screen; or using a touchscreen in which a display screen and a touchpad are integrated; or using a contactless input circuitry in which an optical sensor is used; or using a voice input circuitry. Meanwhile, the input interface 33 can be installed in the gantry 10. Alternatively, the input interface 33 can be configured as a tablet terminal capable of performing wireless communication with the main body of the console 30. The input interface 33 is not limited to include physical operating components such as a mouse and a keyboard. That is, examples of the input interface 33 also include an electrical-signal processing circuitry that receives electrical signals corresponding to input operations from an external input device disposed separately from the console 30, and outputs the electrical signals to the processing circuitry 34.

The processing circuitry 34 controls the overall operations of the X-ray CT apparatus 3a. For example, the processing circuitry 34 implements an acquisition function 341, a transmission-reception function 342, and a control function 343. Herein, for example, the processing functions that are implemented using the acquisition function 341, the transmission-reception function 342, and the control function 343, which represent the constituent elements of the processing circuitry 34 illustrated in FIG. 2, are recorded as computer-executable programs in the memory 31. The processing circuitry 34 is, for example, a processor that reads computer programs from the memory 31 and executes them so as to implement the corresponding functions. In other words, upon reading the computer programs, the processing circuitry 34 gets equipped with the functions as illustrated in the processing circuitry 34 in FIG. 2. Herein, the processing circuitry 34 represents an example of processing circuitry.

Meanwhile, with reference to FIG. 2, the explanation is given about the case in which the processing functions of the acquisition function 341, the transmission-reception function 342, and the control function 343 are implemented by a single processing circuitry 34. However, the first embodiment is not limited to that case. Alternatively, for example, the processing circuitry 34 can be configured by combining a plurality of independent processors, and each of those processors can implement processing functions by executing computer programs. Still alternatively, the processing functions of the processing circuitry 34 can be implemented in a dispersed manner among a plurality of processing circuitry or in an integrated manner in a single processing circuitry.

The acquisition function 341 controls various operations related to the acquisition of CT image data in response to an input operation received from the operator via the input interface 33. More particularly, the acquisition function 341 controls the CT scanning performed in the gantry 10. For example, the acquisition function 341 controls the operations of the X-ray high-voltage generator 14, the X-ray detector 12, the control device 15, the DAS 18, and the couch driving device 22; and controls the CT scanning performed in the gantry 10. More particularly, the acquisition function 341 controls the acquisition operation of acquiring projection data during scanography in which scanograph images (scanogram images) are acquired and during imaging (main scanning) in which the images to be used in diagnosis are acquired; and controls the image generation operation performed based on the projection data.

For example, with respect to the detection data output from the DAS 18, the acquisition function 341 performs preprocessing such as logarithmic transformation, offset correction, inter-channel sensitivity correction, and beam hardening correction; and generates projection data. Moreover, the acquisition function 341 performs a reconstruction operation with respect to the projection data according to the filtered back projection method or the successive approximation reconstruction method; and generates CT image data. Furthermore, the acquisition function 341 implements a known method to convert the CT image data into CT images such as cross-sectional images of an arbitrary cross-sectional surface or rendering-based three-dimensional images.

The transmission-reception function 342 sends a variety of information to and receives a variety of information from the various apparatuses and systems connected to the network 200. More particularly, the transmission-reception function 342 sends the processing result obtained by the X-ray CT apparatus 3a to the various apparatuses and systems connected to the network 200. Moreover, the transmission-reception function 342 receives a variety of information from the various apparatuses and systems connected to the network 200. For example, the transmission-reception function 342 sends the CT image data to the medical image processing apparatus 4. Moreover, the transmission-reception function 342 receives the analysis result from the medical image processing apparatus 4.

The control function 343 performs control to display, in the display 32, a variety of image data stored in the memory 31 and the information related to the analysis result received by the transmission-reception function 342. Moreover, the control function 343 obtains images from the camera 51 and, based on the obtained images, controls the illumination from the projector 52.

Figure 3:
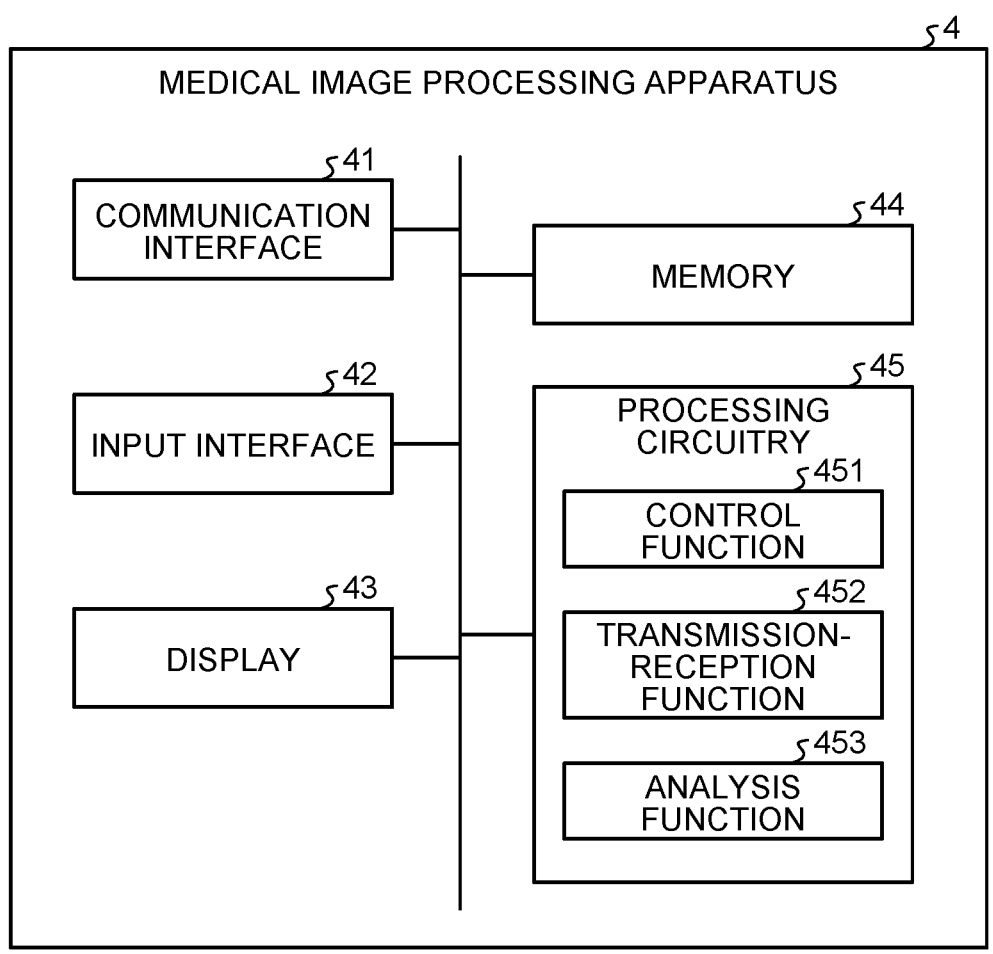
FIG. 3 is a diagram illustrating an exemplary configuration of a medical image processing apparatus according to the first embodiment.

FIG. 3 is a diagram illustrating an exemplary configuration of the medical image processing apparatus 4 according to the first embodiment. The medical image processing apparatus 4 performs a variety of information processing related to the subject. More particularly, the medical image processing apparatus 4 obtains the image data from the medical image diagnostic apparatus 3 via the network 200, and performs a variety of information processing using that image data. For example, the medical image processing apparatus 4 includes a communication interface 41, the input interface 42, a display 43, a memory 44, and a processing circuitry 45.

The communication interface 41 controls the transmission and the communication of a variety of data sent and received between the medical image processing apparatus 4 and the other apparatuses connected via the network 200. The communication interface 41 is implemented using, for example, a network card, a network adaptor, or a network interface controller (NIC).

The input interface 42 receives input operations of various instructions and a variety of information from the operator of the medical image processing apparatus 4. More particularly, the input interface 42 is connected to the processing circuitry 45; and converts the input operations from the operator into electrical signals, and outputs the electrical signals to the processing circuitry 45. The input interface 42 is implemented, for example, using a trackball; or using switches; or using a mouse; or using a keyboard; or using a touchpad for performing input operations by touching an operation screen; or using a touchscreen in which a display screen and a touchpad are integrated; or using a contactless input circuitry in which an optical sensor is used; or using a voice input circuitry. In the present written description, the input interface 42 is not limited to include physical operating components such as a mouse and a keyboard. Alternatively, examples of the input interface 42 also include an electrical-signal processing circuitry that receives an electrical signal corresponding to an input operation from an external input device disposed separately from the device, and outputs the electrical signal to a control circuitry.

The display 43 is used to display a variety of information and a variety of data. More particularly, the display 43 is connected to the processing circuitry 45 and displays a variety of information and a variety of data output from the processing circuitry 45. The display 43 is implemented using, for example, a liquid crystal display, a cathode ray tube (CRT), an organic electroluminescence (EL) display, a plasma display, or a touch-sensitive panel.

The memory 44 is implemented, for example, using a semiconductor memory device such as a random access memory (RAM) or a flash memory; or using a hard disk; or using an optical disk. The memory 44 is used to store, for example, the image data received from the medical image diagnostic apparatus 3. Moreover, the memory 44 is used to store, for example, computer programs that enable the circuitry in the medical image processing apparatus 4 to implement their functions.

The processing circuitry 45 controls the overall operations of the medical image processing apparatus 4. For example, the processing circuitry 45 implements a control function 451, a transmission-reception function 452, and an analysis function 453. Herein, for example, the processing functions that are implemented by the control function 451, the transmission-reception function 452, and the analysis function 453, which represents the constituent elements of the processing circuitry 45 illustrated in FIG. 3, are recorded as computer-executable programs in the memory 44. The processing circuitry 45 is, for example, a processor that reads computer programs from the memory 44 and executes them so as to implement the corresponding functions. In other words, upon reading the computer programs, the processing circuitry 45 gets equipped with the functions as illustrated in the processing circuitry 45 in FIG. 3. Herein, the processing circuitry 45 represents an example of processing circuitry.

Meanwhile, with reference to FIG. 3, the explanation is given about the case in which the processing functions of the control function 451, the transmission-reception function 452, and the analysis function 453 are implemented by a single processing circuitry 45. However, the first embodiment is not limited to that case. Alternatively, for example, the processing circuitry 45 can be configured by combining a plurality of independent processors, and each of those processors can implement processing functions by executing computer programs. Still alternatively, the processing functions of the processing circuitry 45 can be implemented in a dispersed manner among a plurality of processing circuitry or in an integrated manner in a single processing circuitry.

The control function 451 reads data from the memory 44 and performs control to display the data in the display 43. The transmission-reception function 452 sends a variety of information to and receives a variety of information from the various apparatuses and systems connected to the network 200. For example, the transmission-reception function 452 receives the image data from the medical image diagnostic apparatus 3 (for example, the X-ray CT apparatus 3a). Moreover, the transmission-reception function 452 sends the analysis result obtained by the analysis function 453 to the medical image diagnostic apparatus 3 (for example, the X-ray CT apparatus 3a).

The analysis function 453 analyzes, based on the image data received from the medical image diagnostic apparatus 3 (for example, the X-ray CT apparatus 3a), whether or not the subject for whom the image data is acquired is suffering from any disease. For example, the analysis function 453 performs the analysis by running an analysis application such as the computer-aided diagnosis (CADx). As an example, the analysis function 453 quantitatively analyzes the image data and obtains the analysis result about the differential diagnosis of diseases (an infectious disease and an acute disease leading to death if its findings are missed (hereinafter, this is called "killer disease")) (for example, in the differential diagnosis, the probability of existence of particular imaging findings is indicated in a quantified manner). For example, the analysis function 453 runs an analysis application for each body region and for each type of image data, and obtains the analysis result.

Till now, the explanation was given about the configuration of the medical image processing system 100 according to the first embodiment. With such a configuration, the medical image diagnostic apparatus 3, the medical image processing apparatus 4, and the medical image processing system 100 according to the embodiment enable taking appropriate measures after the medical images have been acquired.

At the clinical site, when a disease is predicted to a certain extent due to the clinical condition of the subject, the healthcare professionals can take action in advance and perform examination. However, there are times when the subject has no symptoms but is suffering from a disease such as an infectious disease or a killer disease. In that case, since a medical image diagnostic apparatus is not equipped with the function of determining whether or not the subject for whom the imaging has been performed is suffering from an infectious disease or a killer disease, the measures that are taken remain dependent on the operator performing the examination. That is, if the operator is knowledgeable about the radiographic image interpretation regarding infectious diseases or killer diseases, then it becomes possible to instantly take notice of the key findings. However, in case the operator is not knowledgeable, it may not be possible to take notice of the subject suffering from a disease, and there is a risk of the spread of infection among the healthcare professionals, or the spread of infection in the hospital, or sudden changes in the condition due to the neglect of a killer disease.

In that regard, the medical image diagnostic apparatus 3 (the X-ray CT apparatus 3a) according to the first embodiment sends the acquired image data to the medical image processing apparatus 4; receives the analysis result obtained by analysis applications; and displays warning information based on the analysis result. As a result, it becomes possible to appropriately take measures after the medical images have been acquired.

In the first embodiment, the following explanation is given for the case in which the subject is suffering from an infectious disease. Meanwhile, the operations according to the first embodiment are not applicable to the examination of a subject who is already established to be suffering from an infectious disease even before performing the examination.

Figure 4:
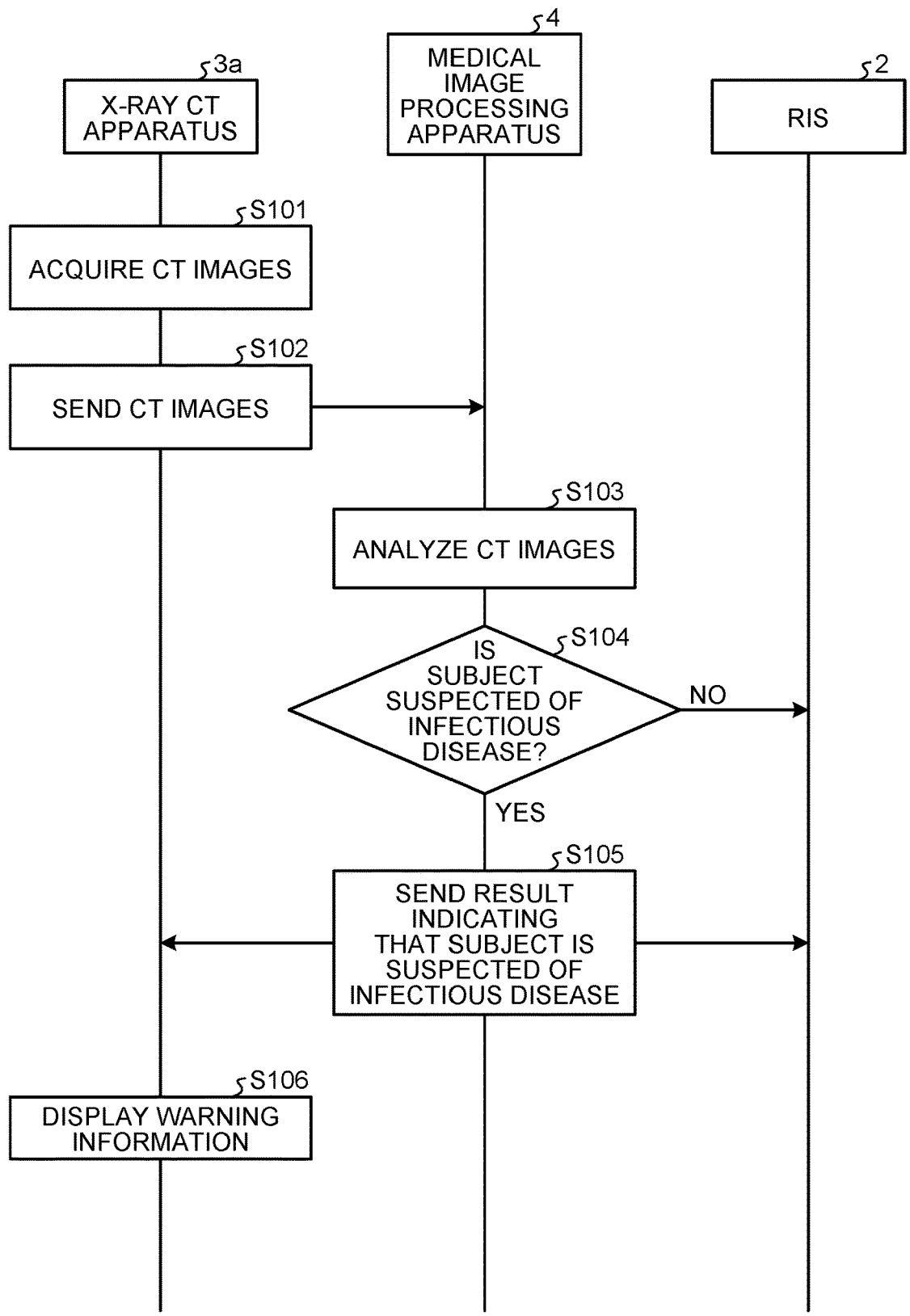
FIG. 4 is a sequence diagram for explaining the flow of operations performed in the medical image processing system according to the first embodiment.

FIG. 4 is a sequence diagram for explaining the flow of operations performed in the medical image processing system 100 according to the first embodiment. The operation at Step S101 illustrated in FIG. 4 is implemented when the processing circuitry 34 reads the computer program corresponding to the acquisition function 341 from the memory 31 and executes it. Moreover, the operation at Step S102 is implemented when the processing circuitry 34 reads the computer program corresponding to the transmission-reception function 342 from the memory 31 and executes it. Furthermore, the operation at Step S106 is implemented when the processing circuitry 34 reads the computer program corresponding to the control function 343 from the memory 31 and executes it. Moreover, the operation at Step S103 is implemented when the processing circuitry 45 reads the computer program corresponding to the analysis function 453 from the memory 44 and executes it. Furthermore, the operations at Steps S104 and S105 are implemented when the processing circuitry 45 reads the computer program corresponding to the transmission-reception function 452 from the memory 44 and executes it.

As far as the transmission and reception of data in the medical image processing system 100 is concerned, each apparatus constantly monitors the data reception and accordingly performs operations. For example, the medical image processing system 100 sends and receives the data illustrated in FIG. 5. FIG. 5 is a diagram for explaining an example of the data sent and received by the medical image processing system 100 according to the first embodiment.

For example, as illustrated in FIG. 5, the data sent and received by the medical image processing system 100 contains the following: a "message ID" in the form of a "data format"; a "source IP" that is compatible to "IPv4" or "IPv6"; a "source apparatus ID/source apparatus name" in the form of a "numerical value/string"; a "destination IP" that is compatible to "IPv4" or "IPv6"; and a "destination apparatus ID/destination apparatus name" in the form of a "numerical value/string". Moreover, as illustrated in FIG. 5, the data sent and received by the medical image processing system 100 contains a flag "Flag urgency" indicating "either urgent, or warning, or info". That is, the data sent and received during the operations illustrated in FIG. 4 is sent and received on priority as compared with other data.

Furthermore, as illustrated in FIG. 5, the data sent and received by the medical image processing system 100 contains "message content" indicating data in the form of a "string"; and contains "concerned examination ID" and "concerned subject ID" in the form of a "character string".

For example, in the medical image processing system 100 according to the first embodiment, as illustrated in FIG. 4, firstly, the processing circuitry 34 of the X-ray CT apparatus 3a acquires CT images (Step S101) and sends them to the medical image processing apparatus 4 (Step S102). The CT images sent from the X-ray CT apparatus 3a can be CT images obtained as a result of the reconstruction operation or obtained as a result of performing image processing with respect to the CT image data.

Upon receiving the CT images from the X-ray CT apparatus 3a, the processing circuitry 45 of the medical image processing apparatus 4 analyzes the CT images (Step S103) and determines whether or not the subject is suspected of an infectious disease (Step S104). More particularly, in response to receiving the CT images, the processing circuitry 45 automatically opens up the analysis applications and uses them to perform analysis for distinguishing the infectious disease. More particularly, based on the data format and the data content of the received data, the processing circuitry 45 selects all analysis applications usable with respect to the received data, and performs analysis using the selected analysis applications.

For example, the processing circuitry 45 selects all applicable analysis applications according to the captured body region and the type of images, and uses the selected analysis applications to perform analysis. As an example, the processing circuitry 45 selects all analysis applications that are applicable with respect to simple CT images of the chest region, and performs the analysis.

Then, depending on the result of analysis performed using the analysis applications, the processing circuitry 45 determines whether or not the subject is suspected of an infectious disease. That is, the processing circuitry 45 determines whether or not the results obtained by all executed analysis applications indicate that the subject is suspected of an infectious disease.

If the subject is not suspected of an infectious disease (No at Step S104), then the processing circuitry 45 sends the analysis result to the RIS 2. On the other hand, if the subject is suspected of an infectious disease (Yes at Step S104), then the processing circuitry 45 sends, to the X-ray CT apparatus 3a and the RIS 2, the result indicating that the subject is suspected of an infectious disease (Step S105). The RIS 2 is used to manage the analysis result, which is received from the medical image processing apparatus 4, in a corresponding manner to the information about the subject.

In the X-ray CT apparatus 3a, when the analysis result is received from the medical image processing apparatus 4, the processing circuitry 34 displays, in the display 32, warning information based on the analysis result (Step S106). More particularly, in the display 32, warning information is displayed to indicate that the subject for whom the CT images were acquired is suspected of a disease. Moreover, based on the images taken by the camera 51, the processing circuitry 34 identifies the positions in the examination room with which the subject and/or the operator came in contact, and illuminates the identified positions with the light from the projector 52.

Figure 6:
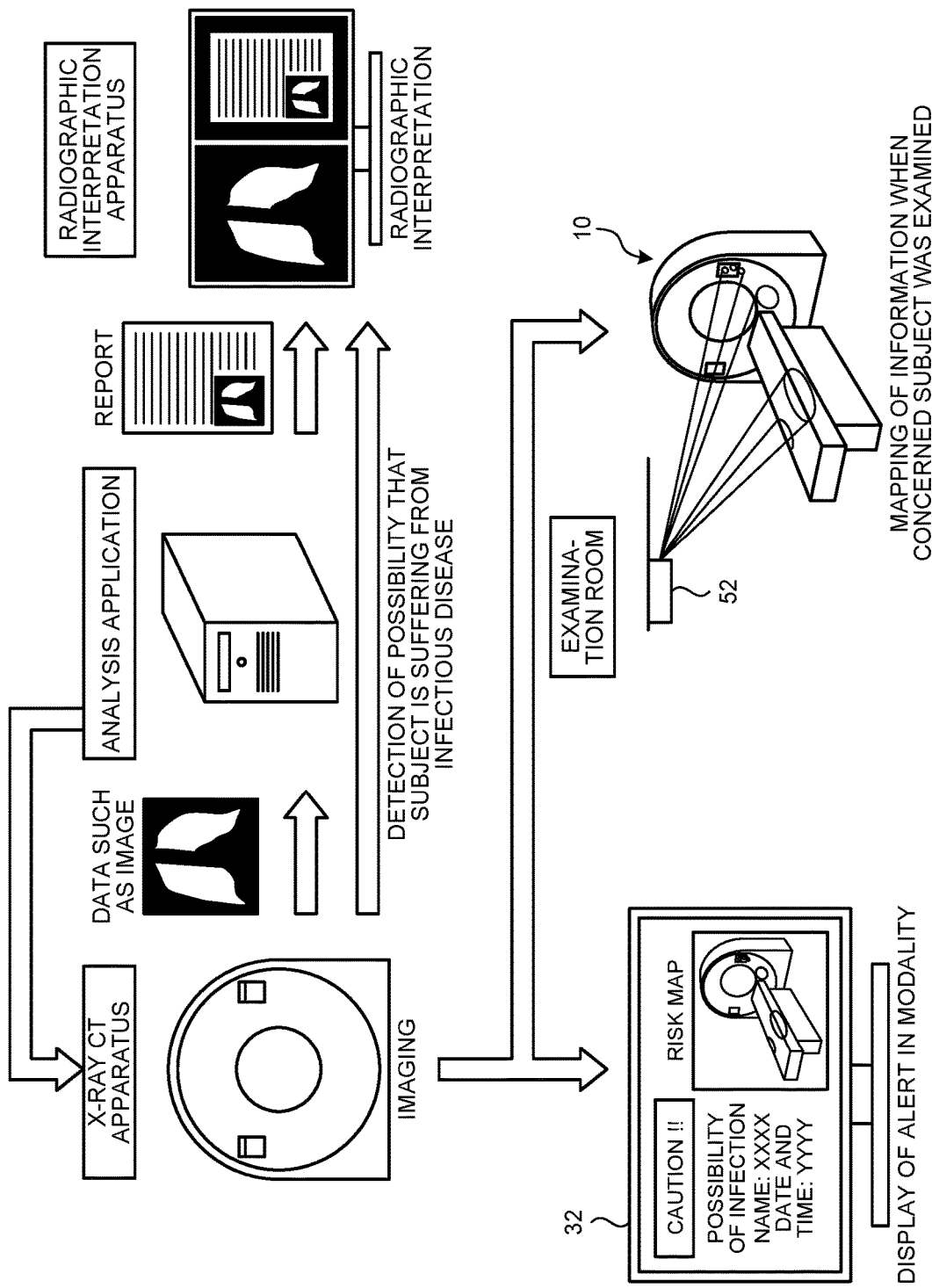
FIG. 6 is a schematic diagram illustrating an example of the operations performed in the medical image processing system according to the first embodiment.

FIG. 6 is a schematic diagram illustrating an example of the operations performed in the medical image processing system 100 according to the first embodiment. For example, in the medical image processing system 100, the X-ray CT apparatus 3a performs imaging, acquires CT images, and sends them to the analysis applications in the medical image processing apparatus 4. At the same time, the X-ray CT apparatus 3a sends the acquired CT images to a radiographic image interpretation terminal.

The analysis applications in the medical image processing apparatus 4 detect the possibility that the subject is suffering from an infectious disease. Than, the medical image processing apparatus 4 sends, to the X-ray CT apparatus 3a, the detected information indicating that the subject is suspected of an infectious disease. At the same time, the medical image processing apparatus 4 sends a report about the analysis result to the radiographic image interpretation terminal.

When the information indicating that the subject is suspected of an infectious disease is received from the medical image processing apparatus 4, the X-ray CT apparatus 3a displays an alert in the display 32. For example, as illustrated in FIG. 6, the processing circuitry 34 of the X-ray CT apparatus 3a displays, in the display 32, an alert indicating the information about the possibility of an infectious disease, the name of the subject, and the date and time.

Moreover, the processing circuitry 34 displays, in the display 32, a risk map as the information indicating the positions in the examination room with which the subject came into contact. For example, the processing circuitry 34 performs control in such a way that, in the external view of the X-ray CT apparatus 3a (for example, a diagram of the apparatus model of the X-ray CT apparatus 3a), the places touched by the subject are displayed in a highlighted manner. Moreover, in addition to the information about the positions with which the subject came into contact, the processing circuitry 34 can also display, as an identical risk map, the information about the positions with which the operator came into contact.

Herein, the processing circuitry 34 can vary the display form of the warning information according to the condition in which the examination is performed. More particularly, depending whether or not the scanning is underway, the processing circuitry 34 varies the display form of the warning information. For example, when the scanning is over, the processing circuitry 34 displays warning information across the entire operation screen of the display 32 as illustrated in FIG. 6. On the other hand, when the scanning is not over, the processing circuitry 34 displays warning information while giving priority to the X-ray irradiation. As an example, during the scanning, the processing circuitry 34 outputs a popup display of the warning information in the top right portion of the operation screen.

Moreover, the processing circuitry 34 performs control in such a way that the places touched by the subject in the examination room are illuminated with the light from the projector 52, so that the contact positions of the subject are explicitly illustrated. For example, as illustrated in FIG. 6, the processing circuitry 34 makes the projector 52 illuminate such positions on the couchtop 23 of the X-ray CT apparatus 3a, which is installed in the examination room, which are touched by hand by the subject. Moreover, as illustrated in FIG. 6, the processing circuitry 34 makes the projector 52 illuminate such positions on the gantry 10 of the X-ray CT apparatus 3a which are touched by hand by the subject. Furthermore, the processing circuitry 34 can perform control also in such a way that, during the examination of the subject, the positions touched by hand by the operator are illuminated with the light from the projector 52.

When the warning information is displayed by the X-ray CT apparatus 3a, the operator becomes able to confirm the information indicating the possibility that the subject is suffering from an infectious disease. As a result, if the subject is still present in the examination room, the operator becomes able to take anti-infection measures as well as take care of the subject. Moreover, the operator can ask the subject to remain in the examination room as may be necessary.

Moreover, once the subject leaves the examination room, the positions illuminated with the light form the projector 52 can be cleaned in a proper manner.

As explained above, according to the first embodiment, the acquisition function 341 acquires CT images. The transmission-reception function 342 sends the CT images to the medical image processing apparatus 4 that performs disease analysis based on medical images, and receives the analysis result from the medical image processing apparatus 4. The display 32 is used to display warning information based on the analysis result. Hence, based on the analysis result, the X-ray CT apparatus 3a according to the first embodiment becomes able to present warning information to the operator present in the examination room, and enables taking appropriate measures after the medical images have been acquired.

Moreover, according to the first embodiment, the display 32 is used to display warning information indicating that the subject for whom medical images are acquired is suspected of a disease (an infectious disease). Hence, the X-ray CT apparatus 3a according to the first embodiment becomes able to present the warning information to the operator, who is present in the examination room, to indicate that the subject is suspected of a disease (an infectious disease); and hence enables taking appropriate measures with respect to the subject suffering from an infectious disease.

For example, even when the operator is not knowledgeable about the radiographic image interpretation, it becomes possible to make the operator recognize the possibility of an infectious disease, so that the risk of infection to the operator can be reduced. Moreover, for example, even when the operator is not knowledgeable about the radiographic image interpretation, it becomes possible to make the operator recognize the possibility of an infectious disease, so that the actions of the subject whose examination is over can be controlled and unnecessary spread of infection can be prevented. Furthermore, it becomes possible to reduce the oversight of the key findings about the subject, thereby enabling therapeutic intervention at an early stage. Moreover, it becomes possible to reduce the oversight of the key findings about the subject, thereby enabling reduction in the litigation risk attributed to the errors made by the healthcare professionals.

Moreover, according to the first embodiment, the display 32 is used to display warning information indicating the area that came in contact with the subject for whom the medical images were acquired. Thus, the X-ray CT apparatus 3a according to the first embodiment enables proper cleaning of the positions that are likely to be contaminated by pathogens, thereby making it possible to hold down the spread of the infection.

Moreover, according to the first embodiment, the transmission-reception function 452 receives medical images acquired by the X-ray CT apparatus 3a. Then, the analysis function 453 performs disease analysis based on the medical images. Subsequently, the transmission-reception function 452 sends the analysis result to the X-ray CT apparatus 3a. Hence, the medical image processing apparatus 4 according to the first embodiment becomes able to present warning information to the operator, who is present in the examination room, to indicate the possibility of the subject suffering from a disease (an infectious disease); and hence enables taking appropriate measures with respect to the subject suffering from an infectious disease.

Second Embodiment

In the first embodiment described above, the explanation is given about the case in which the analysis result indicating that the subject is suspected of an infectious disease is sent to the X-ray CT apparatus 3a. In a second embodiment, the explanation is given about the case in which the analysis result indicating that the subject is suspected of an infectious disease is sent to other medical image diagnostic apparatuses 3. As compared to the first embodiment, in the second embodiment, the operations performed by the transmission-reception function 452 are different. Hence, the following explanation is focused on those operations.

In the analysis result, if it is indicated that the subject for whom the medical images were acquired is suspected of an infectious disease, the transmission-reception function 452 according to the second embodiment sends the analysis result to the other medical image diagnostic apparatuses 3 that were used to examine the subject within a predetermined period of time in the past. For example, the transmission-reception function 452 sends the analysis result, which indicates that the subject is suspected of an infectious disease, to the medical image diagnostic apparatuses 3 that were used to examine the same subject within the last 24 hours.

Figure 7:
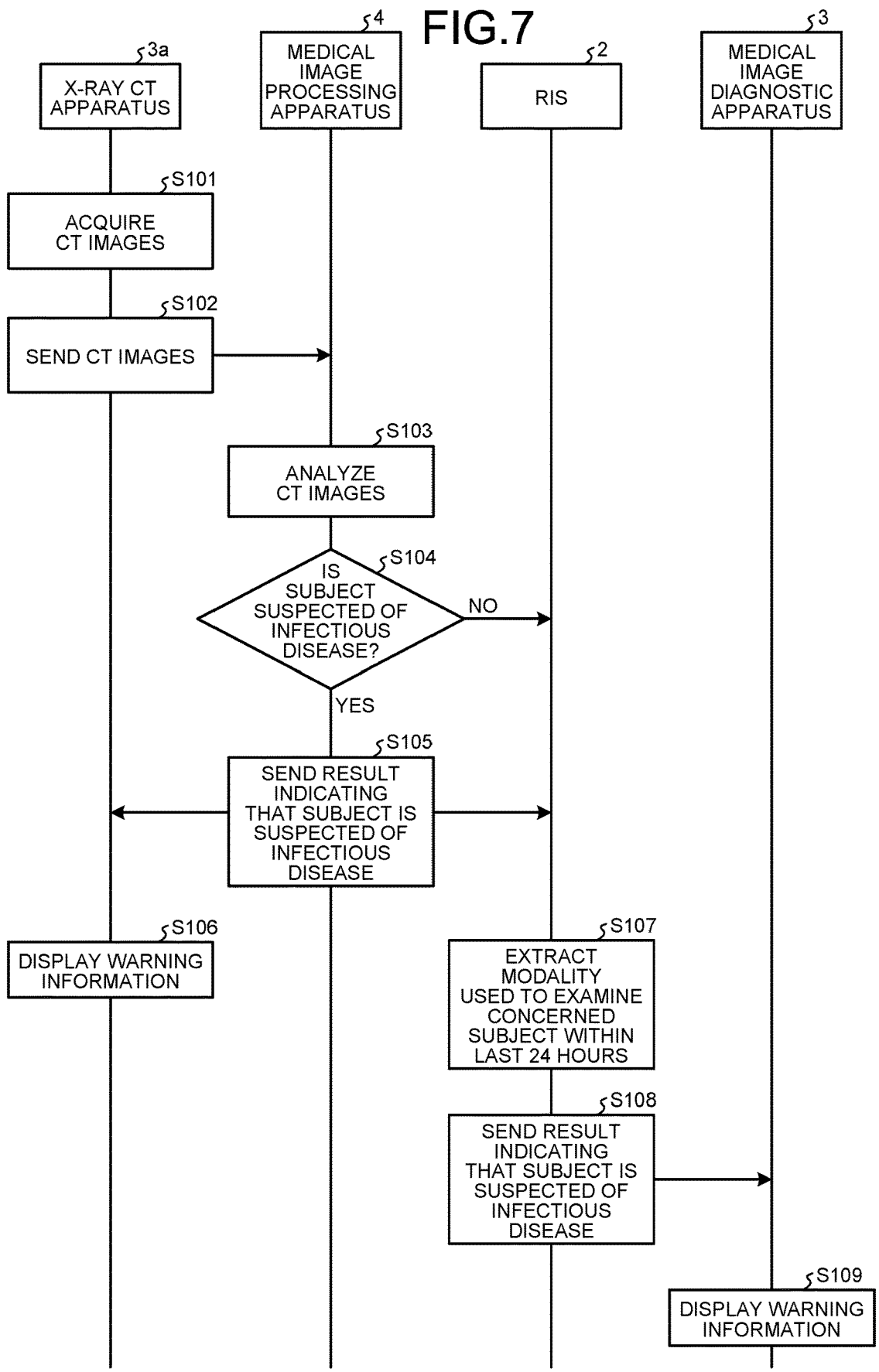
FIG. 7 is a sequence diagram for explaining the flow of operations performed in the medical image processing system according to a second embodiment.

FIG. 7 is a sequence diagram for explaining the flow of operations performed in the medical image processing system 100 according to the second embodiment. In FIG. 7, the operations at Step S107 to Step S109 are added to the flow of operations illustrated in FIG. 4 according to the first embodiment. The operations at Steps S107 and S108 are implemented when the processing circuitry of the RIS 2 reads the corresponding computer program and executes it. The operation at Step S109 is implemented when the processing circuitry of the medical image diagnostic apparatus 3 reads the corresponding computer program and executes it.

For example, in the medical image processing system 100 according to the second embodiment, as illustrated in FIG. 7, firstly, the processing circuitry 34 of the X-ray CT apparatus 3a acquires CT images (Step S101) and sends them to the medical image processing apparatus 4 (Step S102). Upon receiving the CT images from the X-ray CT apparatus 3a, the processing circuitry 45 of the medical image processing apparatus 4 analyzes the CT images (Step S103) and determines whether or not the subject is suspected of an infectious disease (Step S104).

If the subject is not suspected of an infectious disease (No at Step S104), then the processing circuitry 45 sends the analysis result to the RIS 2. On the other hand, if the subject is suspected of an infectious disease (Yes at Step S104), then the processing circuitry 45 sends the result indicating that the subject is suspected of an infectious disease to the X-ray CT apparatus 3a (Step S105). In the X-ray CT apparatus 3a, when the analysis result is received from the medical image processing apparatus 4, the processing circuitry 34 displays, in the display 32, warning information based on the analysis result (Step S106).

Moreover, when the subject is suspected of an infectious disease (Yes at Step S104), the processing circuitry 45 sends, also to the RIS 2, the analysis result indicating that the subject is suspected of an infectious disease. Herein, as a result of sending the analysis result to the RIS 2, the analysis result gets sent to other modalities.

Upon receiving the analysis result from the medical image processing apparatus 4, the RIS 2 extracts the modalities that were used to examine the subject within the last 24 hours (Step S107). For example, based on the subject ID corresponding to the received data, the RIS 2 extracts the modalities that were used to examine the subject within the last 24 hours. Then, the RIS 2 sends, to the extracted modalities, the result indicating that the subject is suspected of an infectious disease (Step S108).

In each other medical image diagnostic apparatus 3 other than the X-ray CT apparatus 3a, upon receiving the analysis result from the RIS 2, the processing circuitry displays, in the display, the warning information based on the analysis result (Step S109). Herein, the processing circuitry of each other medical image diagnostic apparatus 3 either displays the warning information indicating that the concerned subject is suspected of an infectious disease; or identifies the positions in the examination room with which the subject and/or the operator came in contact, and displays the information of the identified positions.

Figure 8:
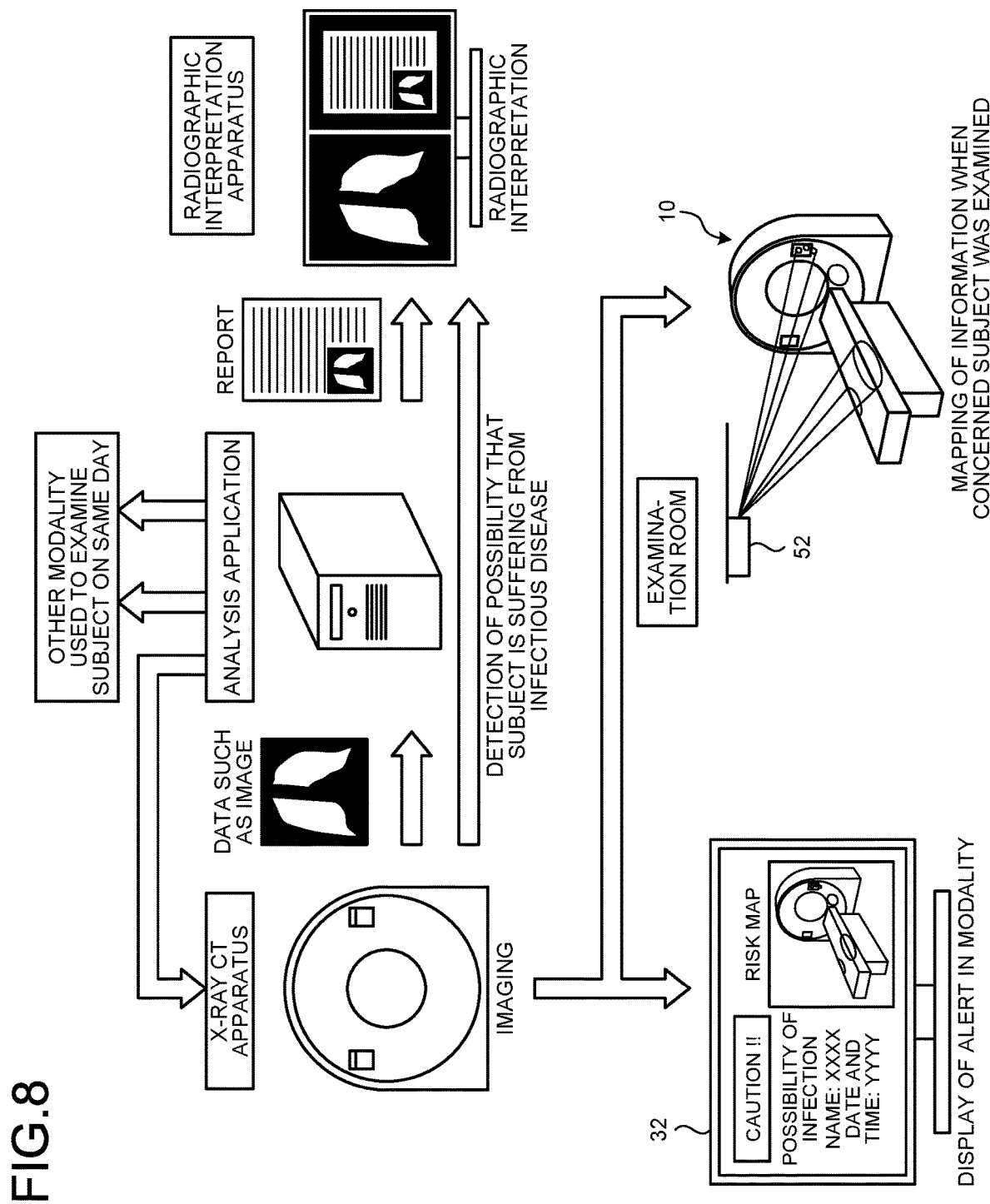
FIG. 8 is a schematic diagram illustrating an example of the operations performed in the medical image processing system according to the second embodiment.

FIG. 8 is a schematic diagram illustrating an example of the operations performed in the medical image processing system 100 according to the second embodiment. For example, as illustrated in FIG. 8, in the medical image processing system 100 according to the second embodiment, when the analysis applications running in the medical image processing apparatus 4 detect the possibility of the subject suffering from an infectious disease, the medical image processing apparatus 4 sends the detected information, which indicates that the subject is suspected of an infectious disease, to the other modalities (the other medical image diagnostic apparatuses 3 other than the X-ray CT apparatus 3a) that were used to examine the subject during that particular day.

When the information indicating that the subject is suspected of an infectious disease is received from the medical image processing apparatus 4, each other medical image diagnostic apparatus 3 other than the X-ray CT apparatus 3a displays an alert in the corresponding display 32. For example, as illustrated in FIG. 6, the other medical image diagnostic apparatuses 3 other than the X-ray CT apparatus 3a displays, in the corresponding display, an alert indicating: the information about the possibility of an infectious disease; the name of the subject; the date and time; and a risk map. Moreover, the other medical image diagnostic apparatuses 3 other than the X-ray CT apparatus 3a can also perform control in such a way that the places touched by the subject in the corresponding examination room are illuminated with the light from a projector, so that the contact positions of the subject are explicitly illustrated.

When the warning information is displayed by the other medical image diagnostic apparatuses 3 other than the X-ray CT apparatus 3a, the healthcare professionals present in the examination room in which that medical image diagnostic apparatus 3 is installed become able to confirm the possibility that the concerned subject is suffering from an infectious disease. As a result, it becomes possible to take measures such as performing cleaning in a proper manner.

Herein, the medical image processing system 100 can also identify other subjects suspected of coming in contact with the subject who is determined to be suspected of an infectious disease. In the medical image processing system 100, the RIS 2 is notified about the execution condition of examination from each modality using the modality performed procedure step (MPPS). For example, regarding the execution condition of examination, the medical image diagnostic apparatus 3 notifies the RIS 2 about the "completed" state, the "discontinued" state, or the "in progress" state.

Thus, the processing circuitry 45 of the medical image processing apparatus 4 sends, to the RIS 2, data containing the information about the suspicion of an infectious disease; and finds out the subjects who were examined subsequent to the subject corresponding to the examination ID and the subject ID specified in that data. Hence, the processing circuitry 45 can identify the other subjects who are suspected of coming in contact with the subject determined to be suspected of an infectious disease.

As explained above, according to the second embodiment, when the analysis result indicates that the subject for whom the medical images were acquired is suspected of an infectious disease, the transmission-reception function 452 sends the analysis result to other medical image diagnostic apparatuses 3 that were used to examine the subject within a predetermined period of time in the past. Hence, the medical image processing apparatus 4 according to the second embodiment becomes able to present the warning information in all medical image diagnostic apparatuses 3 that were used to examine the concerned subject, thereby making it possible to hold down the spread of the infectious disease.

Third Embodiment

In the first and second embodiments, the explanation was given about the case of analyzing the presence or absence of an infectious disease. In a third embodiment, the explanation is given about the case of analyzing the presence or absence of a killer disease. As compared to the first and second embodiments, in the third embodiment, the operations performed by the control function 343 and the analysis function 453 are different. Hence, the following explanation is focused on those operations.

In the medical image processing apparatus 4, the analysis function 453 according to the third embodiment runs analysis applications meant for distinguishing a killer disease, and obtains the analysis result. More particularly, the analysis function 453 runs analysis applications with respect to the CT images received from the X-ray CT apparatus 3a, and analyzes whether or not the subject is suspected of a killer disease. Then, the transmission-reception function 452 sends the analysis result obtained by the analysis function 453 to the X-ray CT apparatus 3a.

In the X-ray CT apparatus 3a, the control function 343 according to the third embodiment displays warning information based on the analysis result in the display 32. More particularly, the display 32 is used to display warning information indicating the possibility that the subject for whom the CT images were acquired is suffering from a killer disease.

Figure 9:
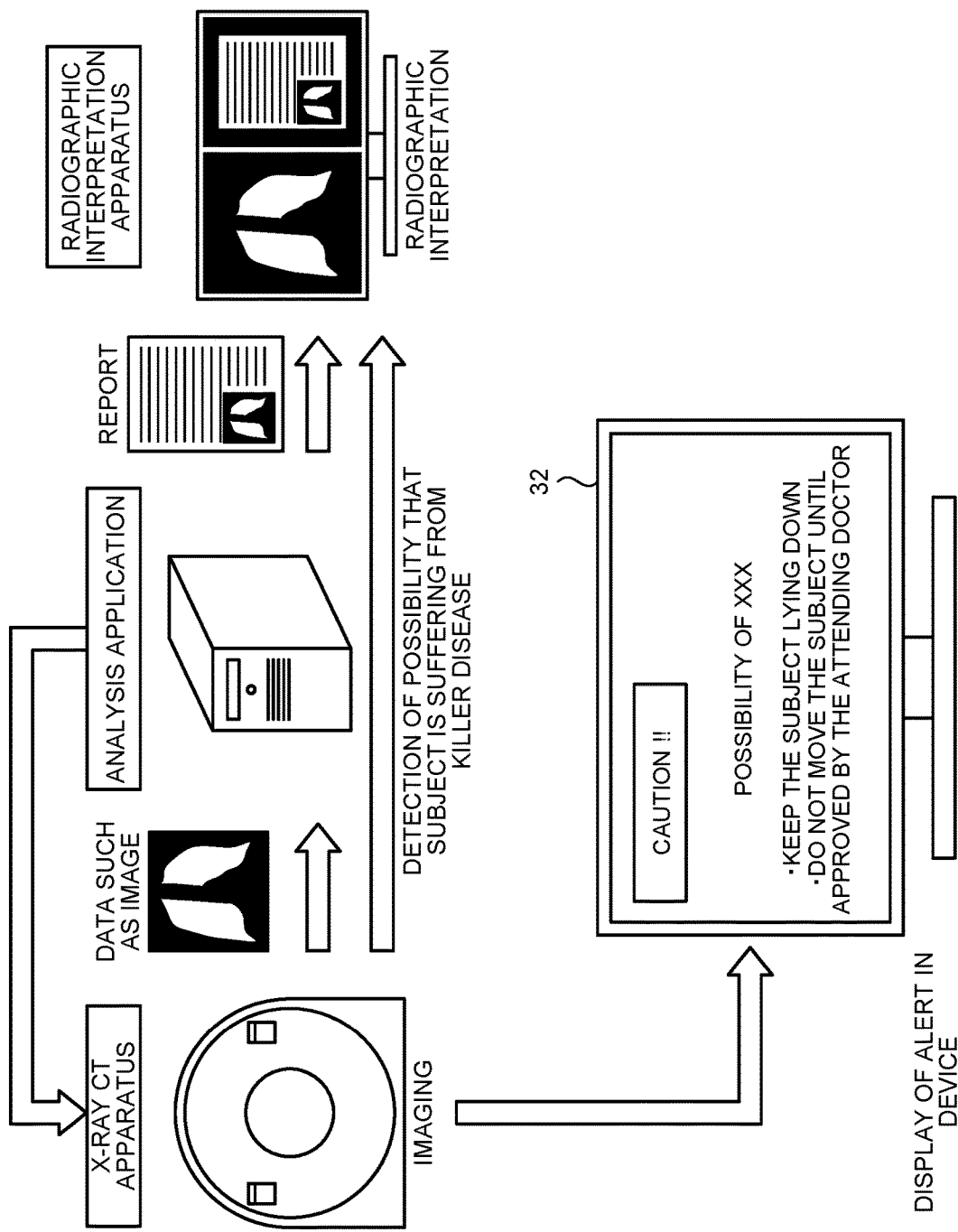
FIG. 9 is a schematic diagram illustrating an example of the operations performed in the medical image processing system according to a third embodiment.

FIG. 9 is a schematic diagram illustrating an example of the operations performed in the medical image processing system according to the third embodiment. For example, in the medical image processing system 100 according to the third embodiment, the X-ray CT apparatus 3a performs imaging, acquires CT images, and sends them to the analysis applications in the medical image processing apparatus 4. At the same time, the X-ray CT apparatus 3a sends the acquired CT images to a radiographic image interpretation terminal.

The analysis applications in the medical image processing apparatus 4 detect the possibility that the subject is suffering from a killer disease. Then, the medical image processing apparatus 4 sends, to the X-ray CT apparatus 3a, the detected information indicating that the subject is suspected of a killer disease. At the same time, the medical image processing apparatus 4 sends a report about the analysis result to the radiographic image interpretation terminal.

When the information indicating that the subject is suspected of a killer disease is received from the medical image processing apparatus 4, the X-ray CT apparatus 3a displays an alert in the display 32. For example, as illustrated in FIG. 9, the processing circuitry 34 of the X-ray CT apparatus 3a displays, in the display 32, the information indicating the possibility of a killer disease and an alert about the measures to be taken with respect to the subject. As an example, the processing circuitry 34 displays, in the display 32, warning information such as "keep the subject lying down" or "do not move the subject until approved by the attending doctor".

When the warning information is displayed by the X-ray CT apparatus 3a, the operator becomes able to confirm the information indicating the possibility that the subject is suffering from a killer disease. As a result, the operator can take measures such as not moving the subject without reason. Moreover, the operator can keep a carrier such as a stretcher ready, and can take actions for avoiding stimulation.

As explained above, according to the third embodiment, the display 32 is used to display the warning information indicating the possibility that the subject for whom the medical images were acquired is suffering from a killer disease. Hence, the X-ray CT apparatus 3a according to the third embodiment becomes able to present, to the operator present in the examination room, the warning information indicating the possibility that the subject is suffering from a killer disease, thereby making it possible to take appropriate measures with respect to the subject suffering from a killer disease.

For example, even if the operator is not knowledgeable about the radiographic image interpretation, it becomes possible for the operator to recognize the possibility of a killer disease, so that the subsequent actions of the subject can be controlled and further deterioration in health conditions can be prevented. Moreover, it becomes possible to reduce the oversight of the key findings about the subject, thereby enabling therapeutic intervention at an early stage. Furthermore, it becomes possible to reduce the oversight of the key findings about the subject, thereby enabling reduction in the litigation risk attributed to the errors made by the healthcare professionals.

Fourth Embodiment

In the third embodiment, the explanation is given about the condition in which the subject who is likely to be suffering from a killer disease has not yet left the examination room. In a fourth embodiment, the explanation is given about the case in which the subject who is likely to be suffering from a killer disease has already left the examination room. As compared to the third embodiment, in the fourth embodiment, the operations performed by the transmission-reception function 342 and the control function 343 are different. Hence, the following explanation is focused on those operations.

Upon receiving the analysis result indicating the possibility that the subject is suffering from a killer disease, the control function 343 according to the fourth embodiment determines whether or not the subject has already left the examination room. For example, when the analysis result indicates that the subject for whom the medical images were acquired is suspected of a killer disease, the information meant for confirming whether or not the subject has already left the examination room is displayed in the display 32. If the subject has already left the examination room, then the transmission-reception function 342 sends information to various apparatuses in the network so as to ensure that the subject does not return home.

Figure 10:
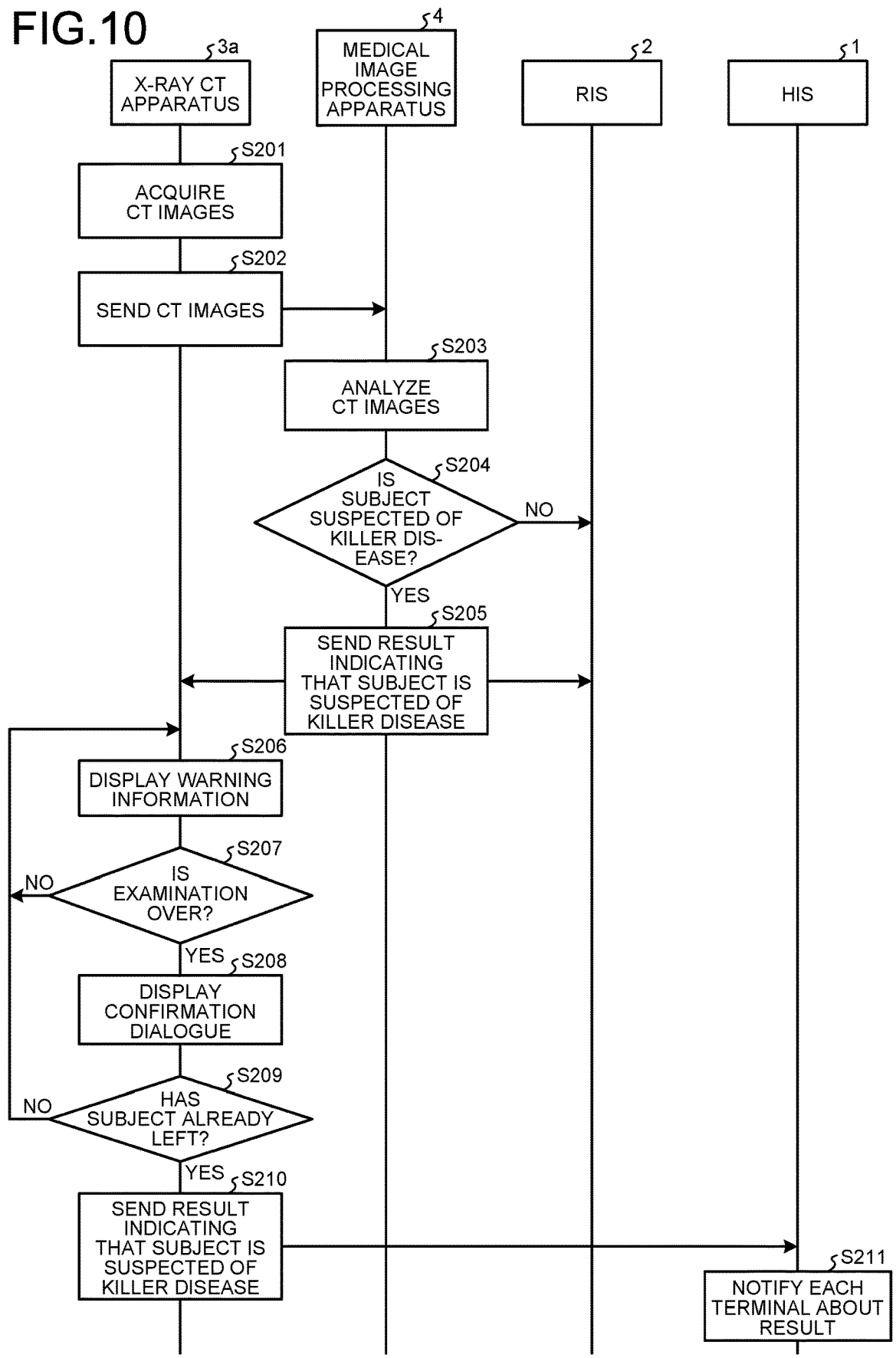
FIG. 10 is a sequence diagram for explaining the flow of operations performed in the medical image processing system according to a fourth embodiment.

FIG. 10 is a sequence diagram for explaining the flow of operations performed in the medical image processing system 100 according to the fourth embodiment. The operation at Step S201 illustrated in FIG. 10 is implemented when the processing circuitry 34 reads the computer program corresponding to the acquisition function 341 from the memory 31 and executes it. Moreover, the operations at Steps S202, S209, and S210 are implemented when the processing circuitry 34 reads the computer program corresponding to the transmission-reception function 342 from the memory 31 and executes it. Furthermore, the operations from Step S206 to Step S208 are implemented when the processing circuitry 34 reads the computer program corresponding to the control function 343 from the memory 31 and executes it. Moreover, the operation at Step S203 is implemented when the processing circuitry 45 reads the computer program corresponding to the analysis function 453 from the memory 44 and executes it. Furthermore, the operations at Steps S204 and S205 are implemented when the processing circuitry 45 reads the computer program corresponding to the transmission-reception function 452 from the memory 44 and executes it. Moreover, the operation at Step S211 is implemented when the processing circuitry of the HIS server of the HIS 1 reads the corresponding computer program from a memory and executes it.

In the transmission and reception of data performed in the medical image processing system 100 according to the fourth embodiment too, each apparatus constantly monitors the reception of the data and accordingly performs operations. For example, the medical image processing system 100 sends and receives the data illustrated in FIG. 5.

For example, in the medical image processing system 100 according to the fourth embodiment, as illustrated in FIG. 10, firstly, the processing circuitry 34 of the X-ray CT apparatus 3a acquires CT images (Step S201) and sends them to the medical image processing apparatus 4 (Step S202). The CT images sent from the X-ray CT apparatus 3a can be CT images obtained as a result of the reconstruction operation or obtained as a result of performing image processing with respect to the CT image data.

Upon receiving the CT images from the X-ray CT apparatus 3a, the processing circuitry 45 of the medical image processing apparatus 4 analyzes the CT images (Step S203) and determines whether or not the subject is suspected of a killer disease (Step S204). For example, the processing circuitry 45 selects all applicable analysis applications according to the captured body region and the type of images, and uses the selected analysis applications to perform analysis.

Then, depending on the result of analysis performed using the analysis applications, the processing circuitry 45 determines whether or not the subject is suspected of a killer disease. That is, the processing circuitry 45 determines whether or not the results of all executed analysis applications indicate that the subject is suspected of a killer disease.

If the subject is not suspected of a killer disease (No at Step S204), then the processing circuitry 45 sends the analysis result to the RIS 2. On the other hand, if the subject is suspected of a killer disease (Yes at Step S204), then the processing circuitry 45 sends, to the X-ray CT apparatus 3a and the RIS 2, the result indicating that the subject is suspected of a killer disease (Step S205). The RIS 2 is used to manage the analysis result, which is received from the medical image processing apparatus 4, in a corresponding manner to the information about the subject.

In the X-ray CT apparatus 3a, when the analysis result is received from the medical image processing apparatus 4, the processing circuitry 34 displays, in the display 32, warning information based on the analysis result (Step S206). More particularly, in the display 32, warning information is displayed to indicate that the subject for whom the CT images were acquired is suspected of a killer disease.

Then, the processing circuitry 34 determines whether or not the examination is over (Step S207). If the examination is not over (No at Step S207), then the processing circuitry 34 continues with the display of the warning information. However, if the examination is already over (Yes at Step S207), then the processing circuitry 34 displays, in the display 32, a confirmation dialogue for confirming whether or not the subject has already left (Step S208); and, according to the input performed in the confirmation dialogue, determines whether or not the subject has already left (Step S209).

If the subject has not yet left (No at Step S209), then the processing circuitry 34 continues with the display of the warning information. However, if the subject has already left (Yes at Step S209), then the processing circuitry 34 sends, to the HIS 1, the result indicating that the subject is suspected of a killer disease (Step S210). When the result indicating that the subject is suspected of a killer disease is received from the X-ray CT apparatus 3a, the HIS 1 notifies the terminal devices included therein about that result (Step S211).

Figure 11:
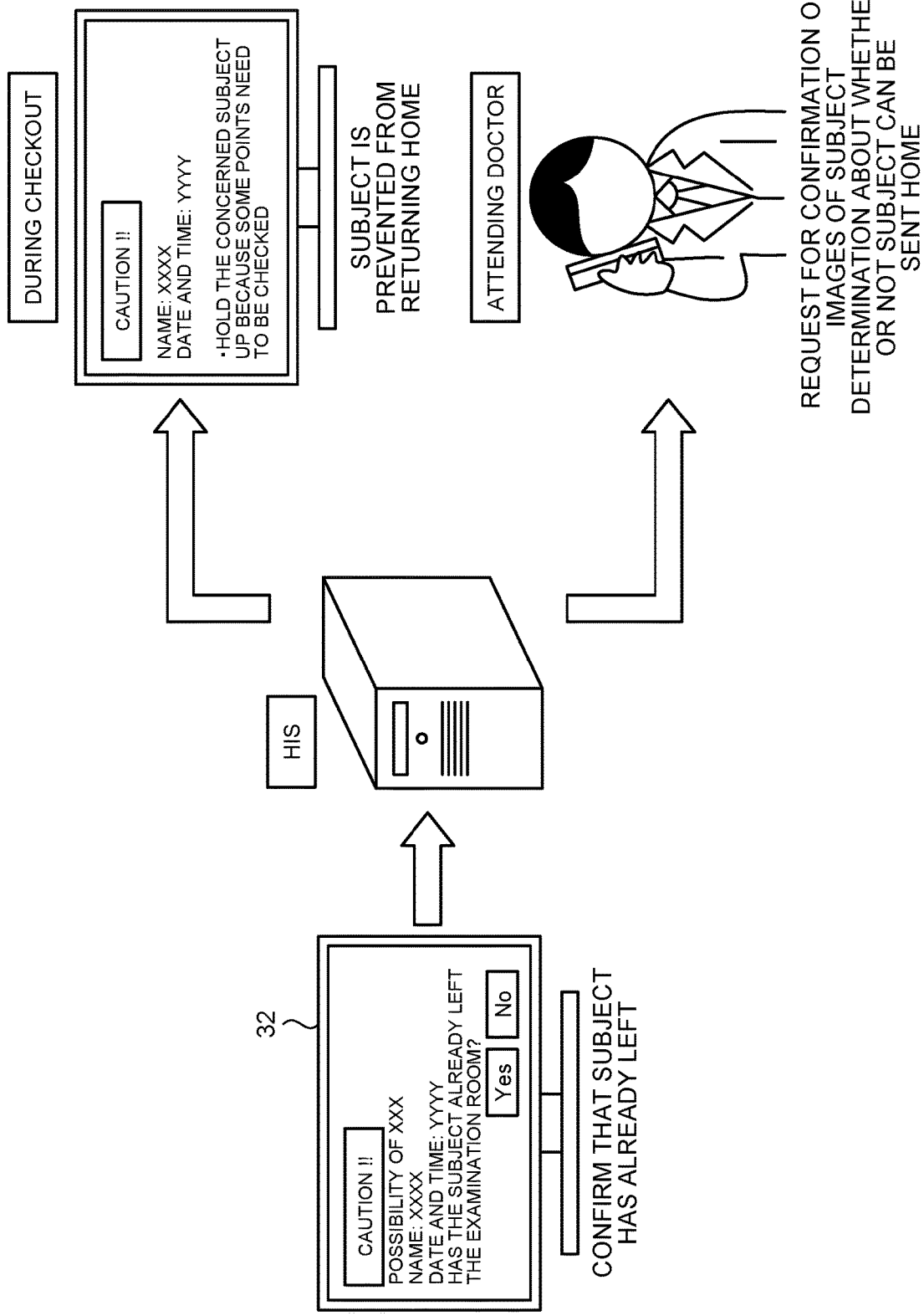
FIG. 11 is a schematic diagram illustrating an example of the operations performed in the medical image processing system according to the fourth embodiment.

FIG. 11 is a schematic diagram illustrating an example of the operations performed in the medical image processing system 100 according to the fourth embodiment. For example, in the medical image processing system 100 according to the fourth embodiment, when the information indicating that the subject is suspected of a killer disease is received from the medical image processing apparatus 4, the X-ray CT apparatus 3a displays an alert in the display 32. Then, if the examination is already over, as illustrated in FIG. 11, the processing circuitry 34 displays, in the display 32, a confirmation dialogue for confirming whether or not the subject has already left; and, according to the input performed in the confirmation dialogue, determines whether or not the subject has already left.

If the subject has already left the examination room, then the processing circuitry 34 sends, to the HIS 1, the information indicating that the subject is suspected of a killer disease. When the information indicating that the subject is suspected of a killer disease is received; as illustrated in FIG. 11, the HIS server of the HIS 1 sends the information indicating that the subject is suspected of a killer disease to, for example, the terminal device that is used at the time of checkout. Moreover, the HIS server displays, in the display of that terminal device, warning information containing the "name", the "date and time" and a message "hold the concerned subject up because some points need to be checked". As a result, the subject is prevented from returning home.

Moreover, as illustrated in FIG. 11, the HIS server issues an image confirmation request to the terminal device of the attending doctor of the concerned subject, and prompts the attending doctor to determine whether or not the subject can be sent home.

As explained above, according to the fourth embodiment, when the analysis result indicates that the subject for whom the medical images were acquired is suspected of a killer disease, the display 32 is used to display information for confirming whether or not the subject has already left the examination room. As a result, the X-ray CT apparatus 3a according to the fourth embodiment becomes able to confirm the whereabouts of the subject who is suspected of a killer disease, and hence enables taking appropriate measures.

Fifth Embodiment

In the first to fourth embodiments, the explanation is given about the case in which the analysis is performed with respect to the CT images that are acquired by the X-ray CT apparatus 3*a* by performing main scanning. In a fifth embodiment, the explanation is given about the case in which analysis is performed with respect to the CT images that are acquired by the X-ray CT apparatus 3*a* by performing scanography. As compared to the first to fourth embodiments, in the fifth embodiment, the operations performed by the analysis function 453 are different. Hence, the following explanation is focused on those operations.

The analysis function 453 according to the fifth embodiment generates analysis images from three-dimensional scanograph images acquired by the X-ray CT apparatus 3*a*, and analyzes the disease based on the analysis images. More particularly, the X-ray CT apparatus 3*a* performs three-dimensional scanography (3D scanning) for deciding on the scanning range of the main scanning. Then, the transmission-reception function 342 of the X-ray CT apparatus 3*a* sends the CT images, which are acquired during the three-dimensional scanography, to the medical image processing apparatus 4.

Figure 12:
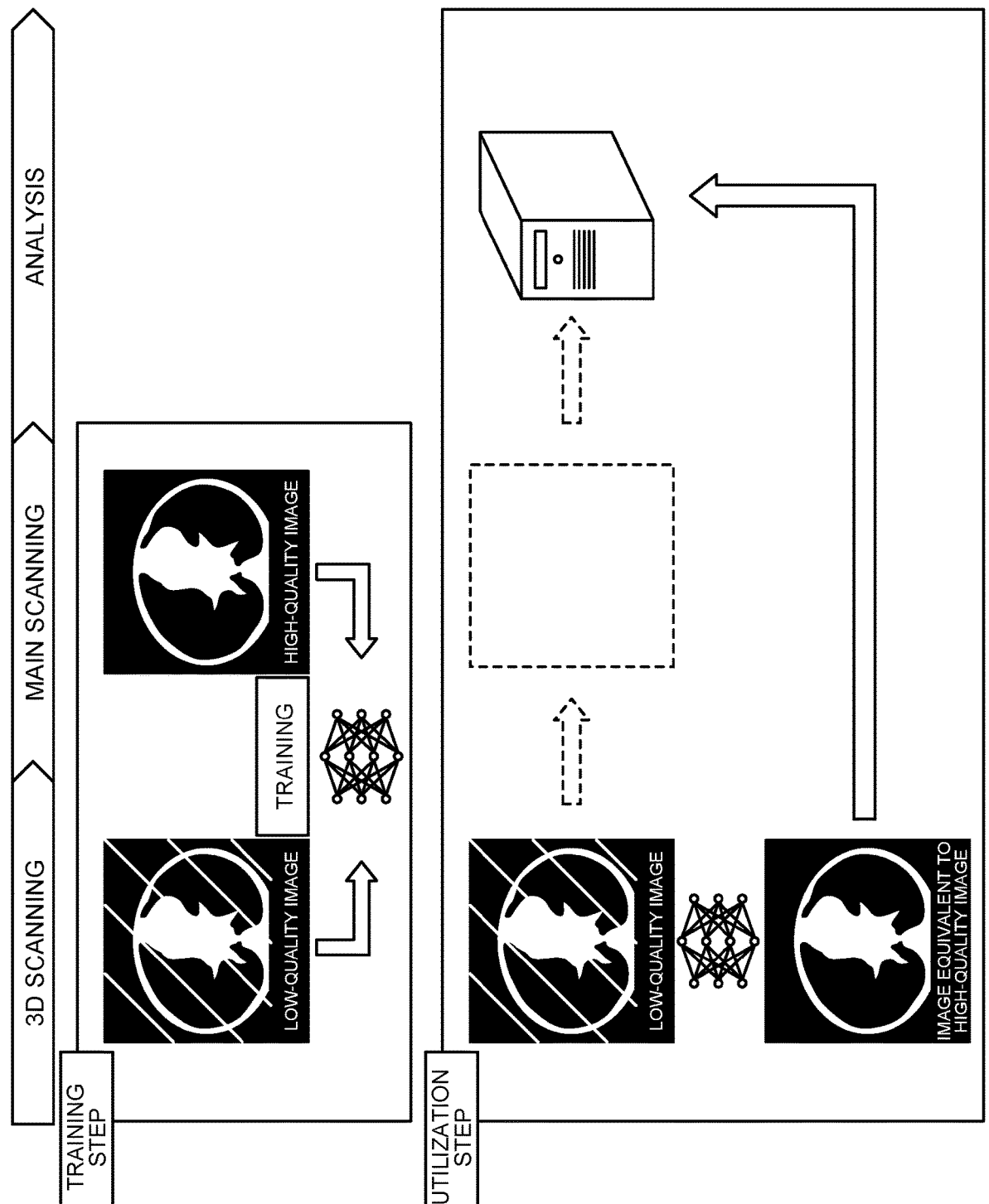
FIG. 12 is a diagram for explaining an example of the operations performed by an analysis function according to a fifth embodiment.

The analysis function 453 generates analysis images from the CT images acquired during the three-dimensional scanography, and runs analysis applications with respect to the generated analysis images. Herein, the analysis function 453 generates the analysis images using, for example, an already-learnt model based on machine learning. FIG. 12 is a diagram for explaining an example of the operations performed by the analysis function 453 according to the fifth embodiment.

For example, as illustrated in a training step in the upper portion in FIG. 12, a CT image obtained by performing 3D scanning (a low-quality image) is treated as an input image, and an already-learnt model is generated by performing, for the number of times equal to a plurality of subjects, machine learning in which a CT image obtained by performing main scanning (a high-quality image) of the concerned subject is treated as the teacher image.

Then, as illustrated in a utilization step in the lower portion in FIG. 12, the analysis function 453 inputs the CT image acquired during 3D scanning to the already-learnt model that is already generated, and generates an analysis image (an image equivalent to a high-quality image). Moreover, the analysis function 453 runs analysis applications with respect to the generated analysis image, and obtains the analysis result to be used in determining the presence or absence of a disease (an infectious disease or a killer disease).

As explained above, according to the fifth embodiment, the analysis function 453 generates analysis images from the three-dimensional scanograph images acquired by the X-ray CT apparatus 3*a*, and analysis the disease based on the analysis images. Hence, as soon as the 3D scanning is performed, the medical image processing apparatus 4 according to the fifth embodiment becomes able to detect an infectious disease or a killer disease, thereby enabling taking measures at an even earlier stage. Moreover, when the medical image processing apparatus 4 is able to perform the analysis using only the CT images obtained during the 3D scanning, there are times when the main scanning is no more required, thereby preventing unnecessary exposure to radiation.

Other Embodiments

In the embodiments described above, the explanation is given about the case in which the X-ray CT apparatus 3*a* is used as the medical image diagnostic apparatus 3. However, the embodiments are not limited to that case, and it is possible to use some other modality such as an X-ray diagnostic apparatus, an MRI apparatus, or an ultrasonic diagnostic apparatus as the medical image diagnostic apparatus 3. In that case, the processing circuitry of the concerned modality performs the operations of sending medical images, receiving the analysis result, and displaying the warning information.

Moreover, in the embodiments described above, the explanation is given about the case in which the transmission of medical images from the medical image diagnostic apparatus 3 to the medical image processing apparatus 4 and opening up of the analysis applications is performed automatically. However, the embodiments are not limited to that case; and, alternatively, the transmission of medical images from the medical image diagnostic apparatus 3 to the medical image processing apparatus 4 and opening up of the analysis applications can be performed manually.

Furthermore, in the embodiments described above, the explanation is given about the case in which the medical image processing apparatus 4 sends the analysis result (the information indicating that the subject is suspected of an infectious disease, or the information indicating that the subject is suspected of a killer disease) to the medical image diagnostic apparatus 3. However, the embodiments are not limited to that case; and, alternatively, the analysis result can be sent to a control device that is installed in the examination room for the purpose of controlling the display.

In that case, the transmission-reception function 452 of the medical image processing apparatus 4 sends the analysis result to a display device that is installed in the room in which the examination is performed using the medical image diagnostic apparatus 3. For example, in the examination room, there are times when a surveillance monitor is installed, or a monitor for displaying the information of the HIS 1 or the RIS 2 is installed. The transmission-reception function 452 sends the analysis result to such monitors so that the warning information is displayed on those monitors. As a result, the medical image processing apparatus 4 enables the healthcare professionals, who are present in the examination room, to extensively confirm the warning information.

Meanwhile, in the embodiments described above, the explanation is given about the case in which the analysis is performed using the analysis applications in the medical image processing apparatus 4. However, the embodiments are not limited to that case; and, alternatively, the analysis can be performed in the medical image diagnostic apparatus 3. In that case, for example, the computer program corresponding to the analysis function 453 is stored in the memory 31 of the X-ray CT apparatus 3*a*. Then, the processing circuitry 34 reads the computer program corresponding to the analysis function 453 from the memory 31 and executes it, so that the operations are performed in an identical manner to earlier explanation of the analysis function 453.

Moreover, in the embodiments described above, the explanation is given about the case in which the acquiring unit, the sending unit, the receiving unit, and the analyzing unit according to the present written description are implemented by the acquisition function, the transmission-reception function, and the analysis function of the processing circuitry. However, the embodiments are not limited to that case. Alternatively, for example, other than using the acquisition function, the transmission-reception function, and the analysis function according to the embodiments; the acquiring unit, the sending unit, the receiving unit, and the analyzing unit according to the present written description can be implemented either using only hardware, or using only software, of using a combination of hardware and software.

Meanwhile, the term "processor" used in the description of the embodiments implies, for example, a central processing unit (CPU), or a graphics processing unit (GPU), or an application specific integrated circuitry (ASIC), or a programmable logic device (such as a simple programmable logic device (SPLD), or a complex programmable logic device (CPLD), or a field programmable gate array (FPGA)). Moreover, instead of storing computer programs in a memory, they can be directly incorporated into the circuitry of a processor. In that case, the processor reads the computer programs incorporated in the circuitry and executes them so that the functions get implemented. Meanwhile, the processors according to the embodiments are not limited to be configured using a single circuitry on a processor-by-processor basis. Alternatively, a single processor can be configured by combining a plurality of independent circuitry, and the corresponding functions can be implemented.

A medical image processing program executed by a processor is stored in advance in a read only memory (ROM) or a memory. Alternatively, the medical image processing program can be recorded as an installable file or an executable file in a non-transitory computer-readable recording medium such as a compact disk read only memory (CD-ROM), a flexible disk (FD), a compact disk recordable (CD-R), or a digital versatile disk (DVD). Still alternatively, the medical image processing program can be stored in a downloadable manner in a computer that is connected to a network such as the Internet. For example, the medical image processing program is configured using modules of the processing functions explained above. As far as the actual hardware is concerned, a CPU reads the medical image processing program from a memory medium such as a ROM and executes it, so that the modules get loaded and generated in a main memory device.

In the embodiments and the modification examples described above, the constituent elements of the device illustrated in the drawings are merely conceptual, and need not be physically configured as illustrated. The constituent elements, as a whole or in part, can be separated or integrated either functionally or physically based on various types of loads or use conditions. The processing functions implemented by the device are entirely or partially implemented by the CPU or by computer programs that are analyzed and executed by the CPU, or are implemented as hardware by wired logic.

Of the processes described in the embodiments, all or part of the processes explained as being performed automatically can be performed manually. Similarly, all or part of the processes explained as being performed manually can be performed automatically by a known method. The processing procedures, the control procedures, specific names, various data, and information including parameters described in the embodiments or illustrated in the drawings can be changed as required unless otherwise specified.

According to at least one of the embodiments described above, it becomes possible to take appropriate measures after the medical images have been acquired.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus, comprising:
processing circuitry configured to
acquire a medical image,
send the medical image to a medical image processing apparatus that performs disease analysis based on the acquired medical image, and
receive an analysis result from the medical image processing apparatus; and
a display configured to display warning information based on the received analysis result, wherein the processing circuitry is further configured to
obtain an image taken by a camera located in an examination room in which the medical image was acquired,
identify, based on the obtained image, a position in the examination room with which a subject and/or an operator came in contact, and
illuminate the identified position with light from a projector.

2. The medical image diagnostic apparatus according to claim 1, wherein the display is configured to display the warning information, which indicates a possibility that the subject, for whom the medical image was acquired, has a disease.

3. The medical image diagnostic apparatus according to claim 2, wherein, when the received analysis result indicates that the subject, for whom the medical image was acquired, is suspected of a disease, the display is configured to display information for confirming whether or not the subject has already left the examination room.

4. The medical image diagnostic apparatus according to claim 3, wherein, when the subject has already left the examination room, the processing circuitry is further configured to send, to an apparatus in a network, information for preventing the subject from returning home.

5. The medical image diagnostic apparatus according to claim 1, wherein the display is configured to display the warning information, which indicates an area with which the subject, for whom the medical image was acquired, came into contact.

6. A medical image processing system, comprising:
the medical image diagnostic apparatus according to claim 1; and
the medical image processing apparatus, which includes other processing circuitry configured to:
receive the medical image acquired by the medical image diagnostic apparatus,
perform the disease analysis based on the received medical image, and
send the analysis result to the medical image diagnostic apparatus.

7. A medical image processing apparatus, comprising:
processing circuitry configured to
receive a medical image acquired by a first medical image diagnostic apparatus,
perform disease analysis based on the received medical image, and
send an analysis result to the first medical image diagnostic apparatus, wherein when the analysis result indicates that a subject for whom the medical image was acquired is suspected of an infectious disease, the processing circuitry is further configured to send the analysis result to a second medical image diagnostic apparatus that was used to examine the subject within a past predetermined period of time.

8. The medical image processing apparatus according to claim 7, wherein the first medical image diagnostic apparatus is an X-ray CT apparatus, and the processing circuitry is further configured to:

generate an analysis image from a three-dimensional scanograph image acquired by the X-ray CT apparatus, and perform the disease analysis based on the analysis image.

9. A medical image processing apparatus, comprising:

processing circuitry configured to receive a medical image acquired by a first medical image diagnostic apparatus, perform disease analysis based on the medical image, and send an analysis result to a display installed in an examination room in which an examination is performed using the first medical image diagnostic apparatus, wherein when the analysis result indicates that a subject for whom the medical image was acquired is suspected of an infectious disease, the processing circuitry is further configured to send the analysis result to a second medical image diagnostic apparatus that was used to examine the subject within a past predetermined period of time.

* * * * *